US00PP18996P2

(12) United States Plant Patent
Bergman

(10) Patent No.: US PP18,996 P2
(45) Date of Patent: Jul. 1, 2008

(54) *CHRYSANTHEMUM* PLANT NAMED 'YORIVENDELL'

(50) Latin Name: *Chrysanthemum×morifolium*
Varietal Denomination: Yorivendell

(75) Inventor: Wendy R. Bergman, Lehigh Acres, FL (US)

(73) Assignee: Yoder Brother's Inc., Barberton, OH (US)

( * ) Notice: Subject to any disclaimer, the term of this patent is extended or adjusted under 35 U.S.C. 154(b) by 0 days.

(21) Appl. No.: 11/705,863

(22) Filed: Feb. 14, 2007

(51) Int. Cl.
*A01H 5/00* (2006.01)

(52) U.S. Cl. ..... Plt./294

(58) Field of Classification Search ..... Plt./294
See application file for complete search history.

*Primary Examiner*—Kent Bell
*Assistant Examiner*—June Hwu
(74) *Attorney, Agent, or Firm*—C. A. Whealy

(57) ABSTRACT

A new and distinct cultivar of *Chrysanthemum* plant named 'Yorivendell', characterized by its upright and uniformly mounded plant habit; freely branching and vigorous growth habit; dark green-colored foliage; uniform flowering response; early flowering habit; seven-week response time; freely flowering habit; daisy-type inflorescences with white-colored ray florets; green-colored immature disc florets; and good postproduction longevity.

1 Drawing Sheet

Botanical designation: *Chrysanthemum×morifolium.*
Cultivar denomination: 'YORIVENDELL'.

BACKGROUND OF THE INVENTION

The present invention relates to a new and distinct cultivar of *Chrysanthemum* plant, botanically known as *Chrysanthemum×morifolium,* commercially grown as a potted *Chrysanthemum* and hereinafter referred to by the name 'Yorivendell'.

The objective of the breeding program is to create new potted *Chrysanthemum* cultivars that are suitable for year-round production with freely branching habit, uniform plant growth habit, good vigor, desirable inflorescence form and floret colors, fast response time and excellent postproduction longevity.

The new *Chrysanthemum* originated from a cross-pollination made by the Inventor in March, 2002, in Salinas, Calif. of a proprietary *Chrysanthemum×morifolium* seedling selection identified as code number YB-A1704, not patented, as the female, or seed, parent with a proprietary *Chrysanthemum×morifolium* seedling selection identified as code number YB-4148, not patented, as the male, or pollen, parent. The new *Chrysanthemum* was discovered and selected in March, 2003, by the Inventor as a single flowering plant within the progeny of the stated cross-pollination in a controlled environment in Fort Myers, Fla. The selection of this plant was based on its uniform plant growth habit, freely branching habit, vigor, desirable inflorescence form and floret colors, fast response time and excellent postproduction longevity.

Asexual reproduction of the new *Chrysanthemum* by vegetative tip cuttings was first connected in Fort Myers, Fla. in June, 2003. Asexual reproduction by cuttings has shown that the unique features of this new *Chrysanthemum* are stable and reproduced true to type in successive generations.

SUMMARY OF THE INVENTION

Plants of the cultivar Yorivendell have not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Yorivendell'. These characteristics in combination distinguish 'Yorivendell' as a new and distinct potted *Chrysanthemum* cultivar:

1. Upright and uniformly mounded plant habit.
2. Freely branching and vigorous growth habit.
3. Dark green-colored foliage.
4. Uniform flowering response.
5. Typically grown as a center-budded or as natural spray type.
6. Early flowering habit, seven-week response time.
7. Freely flowering habit.
8. Daisy-type inflorescences with white-colored ray florets and green-colored immature disc florets.
9. Good postproduction longevity with plants maintaining good substance and color for about four weeks in an interior environment.

Plants of the new *Chrysanthemum* differ from plants of the female parent selection in the following characteristics:

1. Plants of the new *Chrysanthemum* flower about one week earlier than plants of the female parent selection.
2. Plants of the new *Chrysanthemum* and the female parent selection differ in ray floret color as plants of the female parent selection have golden yellow-colored ray florets.

Plants of the new *Chrysanthemum* differ from plants of the male parent selection in the following characteristics:

1. Plants of the new *Chrysanthemum* flower about one week earlier than plants of the male parent selection.
2. Plants of the new *Chrysanthemum* do not produce pollen whereas plants of the male parent selection produce pollen.

Plants of the new *Chrysanthemum* can be compared to plants of the *Chrysanthemum* cultivar Shasta, disclosed in U.S. Plant Pat. No. 9,314. In side-by-side comparisons conducted in Fort Myers, Fla., plants of the new *Chrysanthemum* differed from plants of the cultivar Shasta in the following characteristics:

1. Plants of the new *Chrysanthemum* were taller than plants of the cultivar Shasta.
2. Plants of the new *Chrysanthemum* flowered about one week earlier than plants of the cultivar Shasta.

BRIEF DESCRIPTION OF THE PHOTOGRAPHS

The accompanying photographs illustrate the overall appearance of the new *Chrysanthemum*. These photographs show the colors as true as it is reasonably possible to obtain in colored reproductions of this type. Colors in the photographs may differ slightly from the color values cited in the detailed botanical description which accurately describe the colors of the new *Chrysanthemum*.

The photograph at the bottom of the sheet comprises a side perspective view of typical flowering plants of 'Yorivendell'.

The photograph at the top of the sheet is a close-up view of typical inflorescences of 'Yorivendell'.

DETAILED BOTANICAL DESCRIPTION

The aforementioned photographs and following observations and measurements describe plants grown in Leamington, Ontario, Canada during the autumn in a glass-covered greenhouse and under conditions and practices which approximate those generally used in commercial potted *Chrysanthemum* production. During the production of the plants, day temperatures ranged from about 21° C. to 27° C., night temperatures ranged from about 17° C. to 19° C. and light levels ranged from 4,000 to 6,000 foot candles. Four unrooted cuttings were directly stuck in 15-cm containers, exposed to long day/short night conditions, and pinched about two weeks later. At that time, the photoinductive short day/long night treatments were started. Plants used in the photographs and for the description were center-budded and were about eleven weeks old. In the following description, color references are made to The Royal Horticultural Society Colour Chart, 1995 Edition, except where general terms of ordinary dictionary significance are used. Observations and measurements were taken from a single plants.

Botanical classification: *Chrysanthemum×morifolium* cultivar Yorivendell.

Parentage:

*Female, or seed, parent.*—Proprietary selection of *Chrysanthemum×morifolium* identified as code number YB-A1704, not patented. Male, or pollen, parent: Proprietary selection of *Chrysanthemum×morifolium* identified as code number YB-4148, not patented.

Propagation:

*Type.*—Terminal vegetative cuttings.

*Time to initiate roots.*—About four days at temperatures of about 21° C.

*Time to produce a rooted young plant.*—About ten days at temperatures of about 21° C.

*Root description.*—Fine to thick, fibrous; white in color.

*Rooting habit.*—Freely branching; moderately dense.

Plant description:

*Appearance.*—Herbaceous daisy-type potted *Chrysanthemum* typically grown as a center-budded or as a natural spray type. Stems upright and outwardly spreading giving a uniformly mounded appearance to the plant. Freely branching habit, about four to five lateral branches develop after removal of terminal apex (pinching); dense and full plant habit. Strong and vigorous growth habit.

*Plant height.*—About 31 cm.

*Plant width.*—About 26 cm.

*Lateral branches.*—Length: About 28 cm. Diameter: About 4 mm. Internode length: About 1.8 cm to 2 cm. Strength: Strong. Texture: Pubescent. Color: 137A.

Foliage description:

*Arrangement.*—Alternate, simple.

*Length.*—About 5.5 cm.

*Width.*—About 4.2 cm.

*Shape.*—Palmately lobed.

*Apex.*—Cuspidate to mucronate.

*Base.*—Attenuate.

*Margin.*—Palmately lobed, sinuses between lateral lobes mostly parallel.

*Texture, upper and lower surfaces.*—Fine pubescence; veins prominent on lower surface.

*Color.*—Developing foliage, upper surface: 139A. Developing foliage, lower surface: 137C. Fully expanded foliage, upper surface: 147A; venation, 147B. Fully expanded foliage, lower surface: 147B; venation, 147B.

*Petiole.*—Length: About 1.5 cm. Diameter: About 3 mm. Texture, upper and lower surfaces: Pubescent. Color, upper and lower surfaces: Close to 147B.

Inflorescence description:

*Appearance.*—Daisy-type inflorescence form with ligulate-shaped ray florets. Inflorescences borne on terminals above foliage. Disk and ray florets arranged acropetally on a capitulum. Inflorescence not fragrant, typical of *Chrysanthemum*. Typically grown as a center-budded or as a natural spray type.

*Flowering response.*—Under natural conditions, plants flower in the autumn/winter in the Northern Hemisphere. At other times of the year, inflorescence initiation and development can be induced under short day/long night conditions (at least 13.5 hours of darkness). Early flowering habit; plants exposed to two weeks of long day/short night conditions followed by photoinductive short day/long night conditions flower about seven weeks later.

*Postproduction longevity.*—Inflorescences maintain good color and substance for about four weeks in an interior environment.

*Quantity of inflorescences.*—Freely flowering, about 18 to 20 inflorescences develop per plant.

*Inflorescence bud.*—Height: About 2 cm. Diameter: About 1.4 cm. Shape: Ovoid. Color: Close to 157A.

*Inflorescence size.*—Diameter: About 7.5 cm. Depth (height): About 2.2 cm. Diameter of disc: About 1.5 cm. Receptacle height: About 5 mm. Receptacle diameter: About 1.7 cm. Receptacle color: 146A.

*Ray florets.*—Shape: Ligulate. Orientation: Initially upright, then about 30° from vertical, eventually perpendicular to peduncle. Aspect: Initially incurved, then mostly flat. Length: About 3.7 cm. Width: About 1.2 cm. Apex: Broadly acute. Base: Attenuate; short corolla tube. Margin: Entire. Texture, upper and lower surfaces: Smooth, glabrous; velvety. Number of ray florets per inflorescence: About 30 arranged in about three whorls. Color: When opening, upper and lower surfaces: Close to 155A. Fully opened, upper and lower surfaces: Close to 155D.

*Disc florets.*—Arrangement: Massed at center of receptacle. Shape: Tubular, elongated. Apex: Five-pointed. Length: About 6 mm. Width: About 2 mm. Number of disc florets per inflorescence: About 170. Color, immature: Apex: Close to 145A. Mid-section: Close to 145C. Base: Close to 145D. Color, mature: Apex: Close to 1A. Mid-section: Close to 1B. Base: Close to 145D.

*Phyllaries.*—Number of phyllaries per inflorescence: About 26 arranged in about three whorls. Length: About 7 mm. Width: About 3 mm. Shape: Elliptical. Apex: Acute. Base: Truncate. Margin: Entire. Texture, upper surface: Smooth, waxy. Texture, lower surface: Pubescent. Color, upper and lower surfaces: Close to 146A.

*Peduncles.*—Length: First peduncle: About 6 cm. Fourth peduncle: About 8.7 cm. Diameter (first peduncle): About 2 mm. Angle: About 45° from vertical. Strength: Strong, flexible. Texture: Pubescent. Color: Close to 147B.

*Reproductive organs.*—Androecium: Present on disc florets only. Filament length: About 2 mm. Filament color: Close to 145D. Anther shape: Narrowly oblong. Anther length: Less than 1 mm. Anther color: Close to 150B. Pollen amount: None observed. Gynoecium: Present on both ray and disc florets. Pistil length: About 6 mm. Stigma shape: Bi-parted. Stigma color: Close to 1A. Style length: About 3 mm. Style color: Close to 145D. Ovary color: Close to 157A.

*Seed/fruit.*—Seed and fruit production has not been observed.

Disease/pest resistance: Resistance to pathogens and pests common to *Chrysanthemums* has not been observed on plants grown under commercial conditions.

Temperature tolerance: Plants of the new *Chrysanthemum* have demonstrated good tolerance to low temperatures of about 5° C. and high temperatures of about 38° C.

It is claimed:

1. A new and distinct *Chrysanthemum* plant named 'Yorivendell' as illustrated and described.

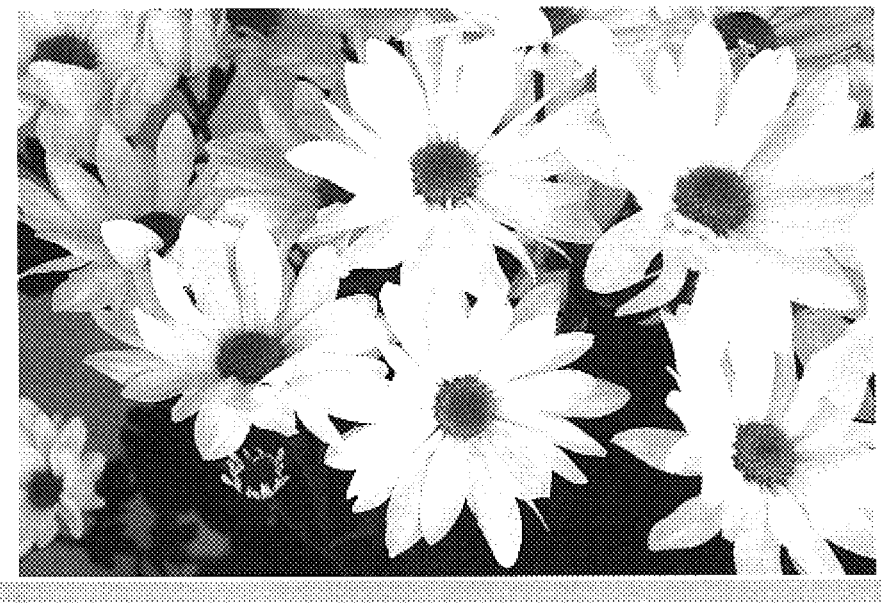
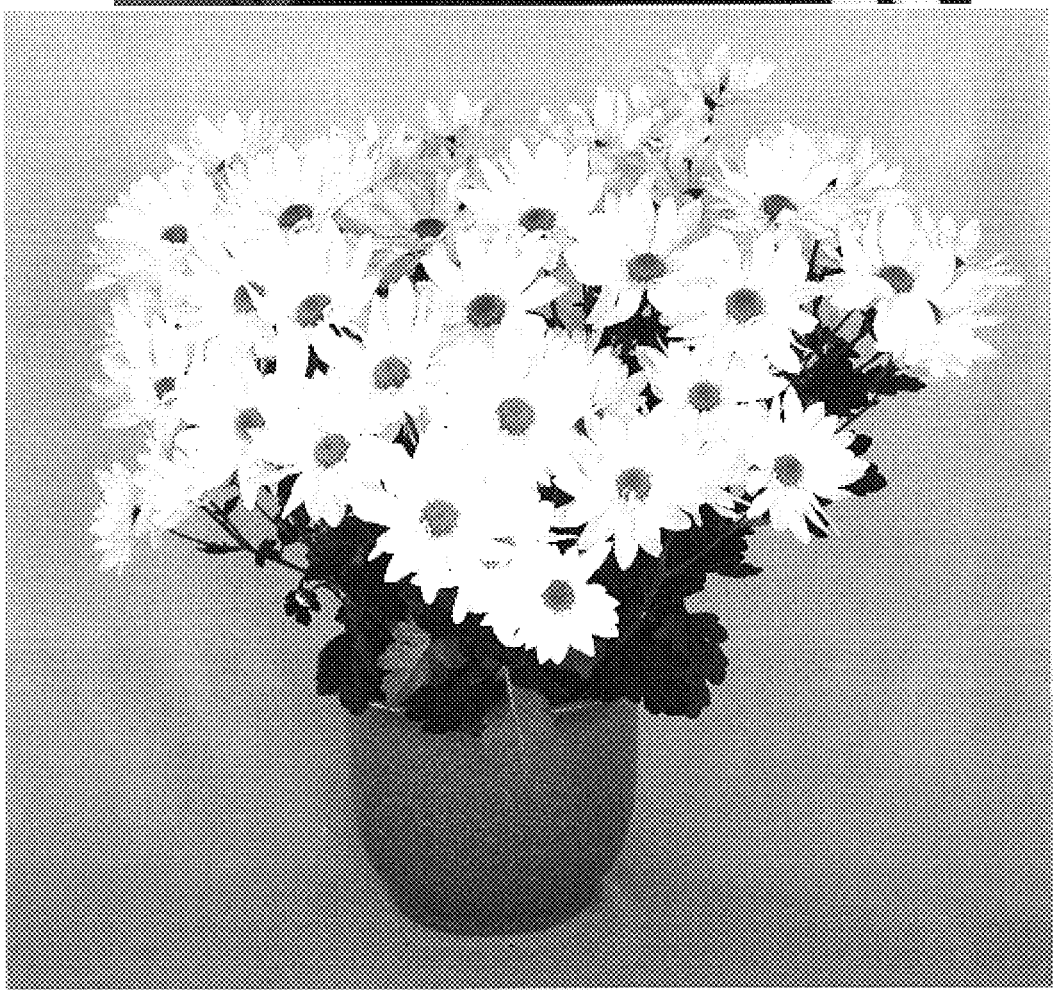

* * * * *